(12) United States Patent
Serrat et al.

(10) Patent No.: US 11,986,969 B2
(45) Date of Patent: May 21, 2024

(54) ROBOT DEVICE FOR GUIDING A ROBOTIC ARM

(71) Applicant: SQUAREMIND, Paris (FR)

(72) Inventors: Tanguy Serrat, Saint-Cloud (FR); Ali Khachlouf, Paris (FR)

(73) Assignee: SQUAREMIND, Paris (FR)

( * ) Notice: Subject to any disclaimer, the term of this patent is extended or adjusted under 35 U.S.C. 154(b) by 0 days.

(21) Appl. No.: 18/010,391

(22) PCT Filed: Jul. 2, 2021

(86) PCT No.: PCT/EP2021/068319
§ 371 (c)(1),
(2) Date: Dec. 14, 2022

(87) PCT Pub. No.: WO2022/003154
PCT Pub. Date: Jan. 6, 2022

(65) Prior Publication Data
US 2023/0191614 A1 Jun. 22, 2023

(30) Foreign Application Priority Data
Jul. 3, 2020 (FR) ....................................... 2007102

(51) Int. Cl.
*B25J 9/16* (2006.01)
*A61B 34/10* (2016.01)
(Continued)

(52) U.S. Cl.
CPC ............. *B25J 9/1697* (2013.01); *A61B 34/32* (2016.02); *G06T 17/00* (2013.01);
(Continued)

(58) Field of Classification Search
CPC ...... B25J 9/1664; B25J 9/1666; B25J 9/1674; B25J 9/1676; B25J 9/1684; B25J 9/1694;
(Continued)

(56) References Cited

U.S. PATENT DOCUMENTS

2008/0033410 A1 2/2008 Rastegar et al.
2016/0191887 A1 6/2016 Casas
(Continued)

FOREIGN PATENT DOCUMENTS

FR 2 917 598 A1 12/2008
FR 3 073 135 A1 5/2019
JP 2013174547 A * 9/2013

OTHER PUBLICATIONS

Zhang, Song, "Recent progresses on real-time 3D shape measurement using digital fringe projection techniques", Apr. 16, 2009, Optics and Lasers in Engineering 48, pp. 149-158 (Year: 2009).*

(Continued)

*Primary Examiner* — Spencer D Patton
(74) *Attorney, Agent, or Firm* — Pillsbury Winthrop Shaw Pittman LLP

(57) ABSTRACT

A robot device ensuring an automatic guiding of a robotic arm, including a frame holding a robotic arm articulated along axes of freedom, the robotic arm including a distal operator device for generating a human-machine interaction, the robot device further including an image acquisition system including at least two optical devices integral with the frame and arranged in at least two distinct positions of the frame, each optical device configured to acquire a 3D image, the image acquisition system being configured to acquire a plurality of 3D images of a human body of a patient from at least two optical devices, the robot device including a calculation unit for generating in real time a human body model of the patient from the acquired 3D images and a guiding trajectory referenced to the surface of the human body model, wherein movements of the robotic arm are enslaved to the guiding trajectory.

15 Claims, 11 Drawing Sheets

(51) Int. Cl.
  *A61B 34/32* (2016.01)
  *G06T 17/00* (2006.01)
  *A61B 90/00* (2016.01)

(52) U.S. Cl.
  CPC ... *A61B 2034/105* (2016.02); *A61B 2034/107* (2016.02); *A61B 2090/371* (2016.02); *G06T 2210/41* (2013.01)

(58) Field of Classification Search
  CPC ....... B25J 9/1697; B25J 13/08; A61B 5/0077; A61B 5/0062–0068; G06T 17/00; G06T 17/20; G06T 17/205; G06T 2201/41
  See application file for complete search history.

(56) References Cited

U.S. PATENT DOCUMENTS

2017/0249729 A1* 8/2017 Greene .................. G06T 7/001
2020/0214568 A1* 7/2020 Vaughan .............. A61B 5/0091
2020/0281667 A1* 9/2020 Blondel ................ A61B 90/13

OTHER PUBLICATIONS

International Search Report as issued in International Patent Application No. PCT/EP2021/068319, dated Oct. 8, 2021.
Written Opinion of the International Searching Authority as issued in International Patent Application No. PCT/EP2021/068319, dated Oct. 8, 2021.

* cited by examiner

ROBOT DEVICE FOR GUIDING A ROBOTIC ARM

CROSS-REFERENCE TO RELATED APPLICATIONS

This application is the U.S. National Stage of PCT/EP2021/068319, filed Jul. 2, 2021, which in turn claims priority to French patent application number 2007102 filed Jul. 3, 2020. The content of these applications are incorporated herein by reference in their entireties.

FIELD

The field of the invention relates to that of robotic devices making it possible to guide an articulated arm in space for treating an area of a body of a patient. More precisely, the field of the invention relates to a device making it possible to enslave the movements of a robotic arm according to an analysis of images acquired in real time.

PRIOR ART

Currently, there is a need to define a device making it possible to diagnose or treat by image analysis or signal transmission an area of a body of a patient, said treatment or said diagnosis being carried out in real time.

One problem with current solutions is that they involve either a significant installation of optical equipment making it possible to obtain images from different points of view in order to reconstitute a complete 3D image of a subject, or to limit all the shots taken by limiting the installation of an optical system with the consequence of limiting the extent of the analysis to maintain real time analysis performance.

In the first case, the system imposes calibration of all the optics and requires implementation of significant image calculation means to generate real time trajectories.

In the second case, the system cannot render a complete view and therefore imposes a complex and longer protocol to diagnose or interact on the surface of a body. One problem then arises of re-establishing an image taking configuration that can be compatible with a previous configuration when the analysis imposes a segmentation of the treatment into several steps of different parts of the subject.

There is a need for a compact solution enabling the reconstruction of the human body of a patient to interact in real time with a robot device.

SUMMARY OF THE INVENTION

The invention detailed below makes it possible to overcome the aforementioned drawbacks.

According to one aspect, the invention relates to a robot device providing the automatic guiding of a robotic arm, comprising a frame holding a robotic arm articulated along a plurality of axes of freedom, said robotic arm comprising a distal operator device for generating a human-machine interaction, said robot device further comprising an image acquisition system comprising at least two optical devices integral with said frame and arranged in at least two distinct positions of the frame, each optical device being configured to acquire a 3D image, the image acquisition system being configured to acquire a plurality of 3D images of a human body of a patient from at least two optical devices, the robot device comprising a calculation unit for generating in real time a human body model of said patient from said acquired 3D images and a guiding trajectory referenced to the surface of said human body model, the movements of said robotic arm being enslaved to said guiding trajectory.

One advantage is to obtain a sufficient field of view for guiding a robot arm on the surface of a human body. The arrangement of a dual 3D camera system on the same frame makes it possible to obtain a reliable reference for the calibration of the optical system and the robot arm.

According to one embodiment, the image acquisition system comprises at least 4 optical devices integral with said frame and arranged in at least 4 distinct positions of said frame. According to one embodiment, the image acquisition system comprises at least 6 optical devices integral with said frame and arranged in at least 6 distinct positions of said frame. According to an exemplary embodiment, each optical device is configured to acquire a 3D image. One advantage of the multiplication of optical devices is to generate as complete a point cloud as possible of the surface of the body of a patient. A second advantage resides in the multiplication of points of view and therefore the reduction of obstruction effects of objects that may be located between the robot and the capture system, it may be the robot itself, the arms of an operator, etc. According to an exemplary embodiment, the optical devices are deactivatable individually or in pairs. For example, an actuator or tactile instruction makes it possible to deactivate the lower optical devices located at the level of the lower part of the frame when the patient is in a lying down position.

According to one embodiment, at least one first optical device comprises a first linear arrangement of at least two cameras along a first axis. According to one embodiment, at least one second optical device comprises a second linear arrangement of at least two cameras along a second axis, said first axis and said second axis being non-colinear with each other. One advantage is to make it possible to generate a field of view suited to generating a modeling of a body of a standing patient, taking into consideration the size of the individual and their stature. According to one embodiment, they are not co-linear with each other.

According to one embodiment, at least one optical device comprises a means of orienting the acquisition axis by actuating a pivot link.

According to one embodiment, each optical device comprises:
- at least two infrared cameras and/or;
- at least one color camera and/or;
- at least one pair of color cameras configured to generate 3D images by stereoscopy and/or;
- at least three cameras comprising two infrared cameras and one color camera and/or;
- at least one infrared projector projecting a pattern and two infrared cameras capturing said pattern projected onto the surface of a human body.
- at least one light projector projecting patterns of structured light and at least one camera capturing said patterns; and/or
- a time-of-flight camera and/or;
- a laser transceiver device.

According to one embodiment, the optical system comprises:
- a first set of optical devices comprising a first field of view between 30° and 70° vertically and between 50 and 100° horizontally; and
- a second set of optical devices comprising a second field of view between 50° and 100° vertically and between 30 and 70° horizontally.

One advantage is to reduce the occlusion generated by displacements of the robot arm in front of the optical system capable of generating shadows. According to one embodiment, each optical device comprises a rectangular field of view.

According to one embodiment, the optical devices are arranged to cover a field of view related to the optical system having a virtual origin displaced out of plane comprising the origins of the optical devices. Thus, in being located behind the optical origins, i.e. further away from the subject, the origin of the virtual field of view offers the possibility of optimizing the construction of an optical field. It is possible to obtain a virtual field of view having a coverage allowing a wider or more separate view thanks to an arrangement of the optical devices distant from each other. One advantage is to make it possible to acquire images of a patient in a standing or lying down position.

According to one embodiment, at least two optical devices are distanced in a horizontal plane of a Cartesian coordinate system by a distance comprised within the range [30 cm and 100 cm]. According to one embodiment, at least two optical devices are distanced along a vertical axis of a Cartesian coordinate system by a distance comprised within the range [30 cm and 100 cm]. One benefit is to cover a large surface, to multiply the points of view and to reduce noise and occlusions causing incomplete acquisitions.

According to one embodiment, the optical devices are arranged to cover a field of view covered by a solid angle of a value greater than or equal to 3·pi/2.

According to one embodiment, the frame comprises a screen making it possible to display a 3D image of a body of an individual from at least one optical device. One advantage is to position a patient optimally by having a direct return of his position on the screen. Another advantage is to carry out calibration operations or adjustments of the orientations of the optical devices. According to one embodiment, this display is created in real time in order to represent the image of the patient and therefore his positioning in space on the screen.

According to one embodiment, the frame comprises a main body and a base, said main body holding the optical system and said base being provided with means of displacement to make the robot device moveable.

According to one embodiment, the base comprises a counterweight, a plurality of casters, and at least one operable brake to stabilize said robot device at a fixed position. One advantage is to enable flexibility of positioning of the robot device in numerous locations and which does not require pre-installation of an optical system and operating console.

According to one embodiment, the frame comprises means for pivoting the main body with respect to the base and a means for blocking the pivoting of said main body so as to orientate said main body with respect to the base at a desired angle.

According to one embodiment, the main body comprises symmetrical wings on either side of the vertical axis of the main body to hold the acquisition devices, at least one wing comprising a handle. One advantage is to increase the scope of the robot device at the level of the positioning of the optics in order to widen the field of view of the optical system.

According to one embodiment, the robot device comprises at least one electronic device to generate from the images acquired by the acquisition system a point cloud representing a three-dimensional surface of the body of a patient. One advantage is to generate data that can be easily processed by a neural network or any other algorithm so that the latter can generate a point cloud, a three-dimensional mesh, or a 3D model of a body, easily exploitable to guide a robot arm.

According to one embodiment, the electronic device generates a global point cloud from a plurality of point clouds generated from each 3D image acquired by each optical device, said global point cloud comprising a compilation of points of each point cloud. One advantage is to fill the portions of point clouds of the human body not acquired by an optical device due to an occlusion of its field of view on a portion of the space. Another advantage is that the portion of the body of a patient that will be modeled is extended as much as possible.

According to one embodiment, the robotic arm comprises at least 5 portions, each portion extending along an axis and pivoting with respect to at least one axis of another portion by means of a pivot link, the pivoting of all the pivot links driving a kinematic of the robotic arm. One advantage is to enable a wide range of applications, notably in dermatology or tattoo treatment applications and, more generally, applications in the non-invasive and invasive medical field.

According to one embodiment, the electronic device generates from the images acquired by the acquisition system instructions for guiding the kinematics of the robotic arm.

According to one embodiment, the electronic device generates a first 3D model of a surface of all or part of a human body, said first 3D model comprising a mesh, said first 3D model being used to calculate a first guiding trajectory on the surface of the first 3D model, and to calculate a first kinematic of the robotic arm. One advantage is to generate a model of the body of a patient to plan a trajectory with a view to a displacement and a guiding of the robot arm.

According to one embodiment, the electronic device generates in real time, from the images acquired by the acquisition system, a new 3D model of a surface of all or part of a human body, said 3D model comprising a mesh, said 3D model generated at regular times being used to recalculate in real time a new guiding trajectory on the surface of the 3D model, and to recalculate in real time a new kinematic of the robotic arm. One advantage is to update the trajectory calculation, notably in a time interval of less than 30 ms.

According to one embodiment, the electronic device comprises self-calibration of the optical devices of the acquisition system with respect to a reference optical device of said acquisition system. The reference device may advantageously be chosen as a calibration reference for positioning the robot arm. Thus, the point clouds are reported in a same common coordinate system thanks to the different geometric transformations calculated by a calibration process.

BRIEF DESCRIPTION OF THE FIGURES

Other characteristics and advantages of the invention will be become clearer on reading the following detailed description, with reference to the appended figures, that illustrate.

The robot device 1 of the invention aims to allow interaction of an articulated robotic arm 6 with a human body 100. The interaction is ensured by a distal operator device 8 of the robotic arm 6 and corresponds, for example, to the transmission of a signal, the taking of an image or the generation of a haptic contact on the skin. Other interactions with the surface or at a depth close to the surface of a body of a patient are possible. The robot device of the invention allows space-guided movements of the articulated robotic arm 6 to allow interaction on all or part of the human body according to a predefined schedule.

One objective of the invention is to enable images of a human body 100 to be acquired according to a suitable field of view to generate a human body model in order to guide the robotic arm 6 in real time. This objective is achieved by the invention notably through an optimized arrangement of an image acquisition system 3'. For this purpose, a compact and mobile robot device 1 is described. Such a robot device 1 comprises, for example, means of stabilizing the robot device 1 to ensure a reliable reference point and mobility of components, such as optics or an articulated arm 6, of said robot device 1 offering a wide variety of configurations of uses.

In addition, an advantage of the invention is to provide a removable robot device 1 that can be quickly deployed according to different configurations of use and having small bulk.

Figure 1:
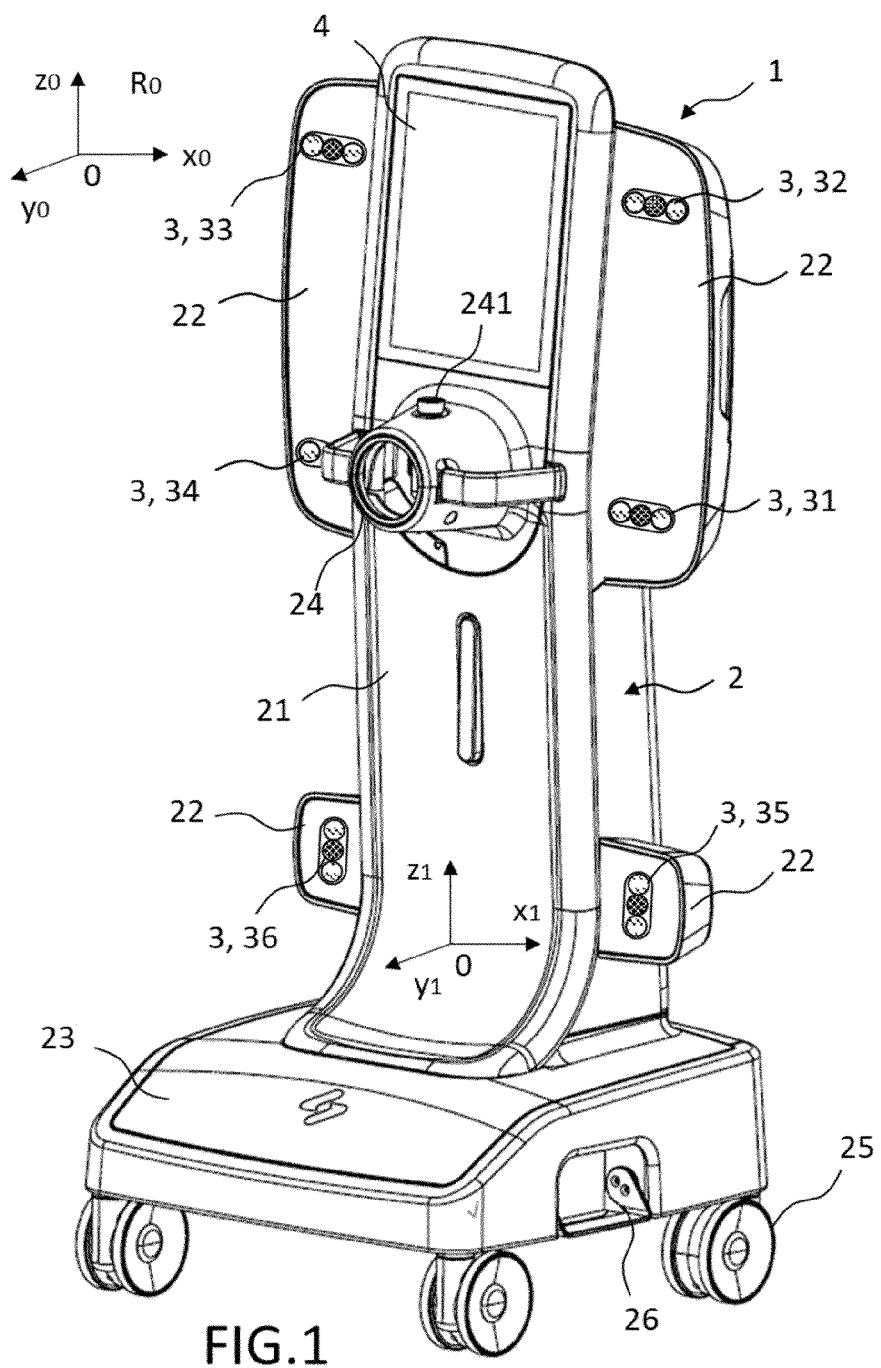
FIG. 1: a robot device according to one embodiment of the invention without articulated robotic arm.

FIG. 1 represents one embodiment of a robot device 1 of the invention.

According to one embodiment, the frame 2 of the robot device 1 of the invention comprises an upper part 21 comprising a mounting bracket 24 of a robotic arm 6, a screen 4, an image acquisition system 3' comprising at least two optical devices 3. In the embodiment of FIG. 1, 6 optical devices 31, 32, 33, 34, 35, 36 are represented. In addition, the robot device 1 comprises a lower part forming a base 23 supporting the upper part 21 and making it removable.

According to one embodiment, the robot device 1 of the invention comprises a plurality of robotic arms 6. In this case, for example, they are fastened to different mounting brackets 24 of the same frame 2.

Base—Means of Displacement

According to this embodiment, the robot device 1 comprises a frame 2 removable in space thanks to a means of displacement represented in FIG. 1 by a plurality of casters 25 fastened to a base 23 of said frame 2. According to alternative embodiments, the means of displacement may alternatively be guided rails in predefined grooves of a floor or wall surface or conversely grooves cooperating with rails arranged on a floor or wall surface. According to an example of this alternative embodiment, rails arranged horizontally along a wall or partition have a curved profile making it possible to maintain the robot arm 1 and move it around a 90° angle portion. If the robot device 1 is displaceable along a vertical wall, the robot device 1 of the invention may not comprise a base and only an upper part 21. Therefore, it may not be in contact with the ground in certain embodiments. According to one embodiment, the robot device 1 is fixed to the wall, for example, by means of a clip, screws or any other fastening means.

According to another example, the means of displacement is a felt arranged on the lower surface of the base 23 so as to allow the base 23 to slide on a smooth floor. According to another embodiment, the means of displacement is a cushion of air propelled by means of a command for a predefined time and making it possible to displace the robot device 1. Finally, according to another example, the means of displacement is a set of microbeads allowing rolling of the robot device 1 while limiting friction.

Brakes

According to one embodiment, the base 23 comprises a brake 26 making it possible to block the displacement of the base 23. The brake 26 notably allows the wheels 25 to be held in a fixed position. It is preferably positioned on the base 23, notably when the robot device 1 can be displaced, for example thanks to a means of displacement located on the base 23. The brake 26 further makes it possible to slow down the speed of displacement of the robot device 1 when it is actuated during its movement. According to an example, the base 23 comprises a plurality of brakes 26 making it possible to stabilize the robot device 1. According to an exemplary embodiment, in order to stabilize the robot device 1, the base 23 comprises a stabilizer. The stabilizer can be activated when the brake 26 is actuated. It makes it possible, for example, to anchor the base 23 to the ground. This stabilizer can be implemented by suction cups, the deployment of a mass in contact with the ground, a contact element with the bearing surface such as a stand or an actuator making it possible to lock the blocking of the wheels. According to one embodiment, deployable stabilization studs make it possible to maintain the robot device 1 of the invention in a fixed position.

When the robot device 1 is held on a vertical wall, such as a wall or partition, the brake 26 can be arranged on the base 23 or the upper part 21. It makes it possible to lock the position of the robot device 1 at a given position of the wall. The brake 26 may take the form of a clamping screw, a clip making it possible to lock the position of the robot device 1 in a groove or other forms.

Mounting Bracket

Figure 2:
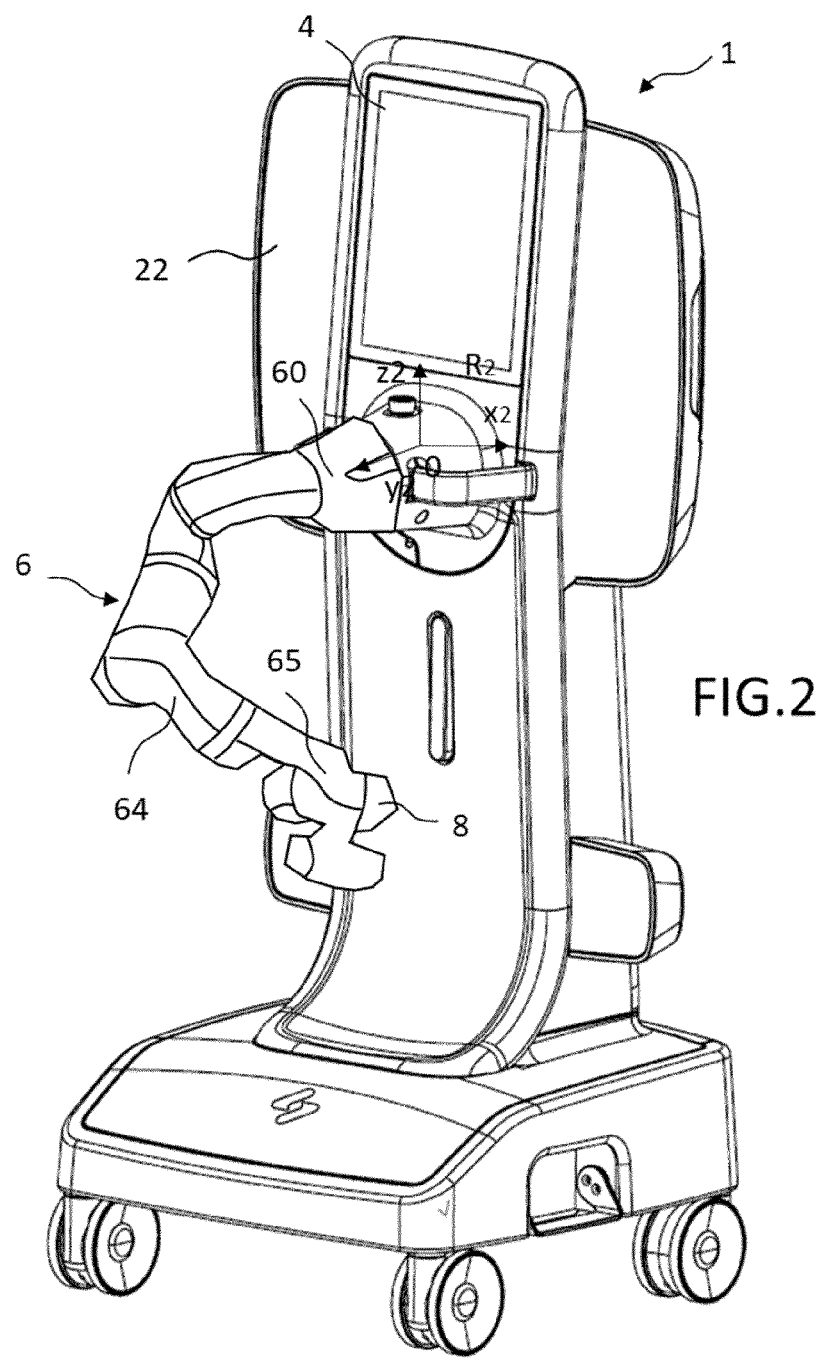
FIG. 2: a robot device according to one embodiment of the invention provided with an articulated robotic arm.
Figure 3:
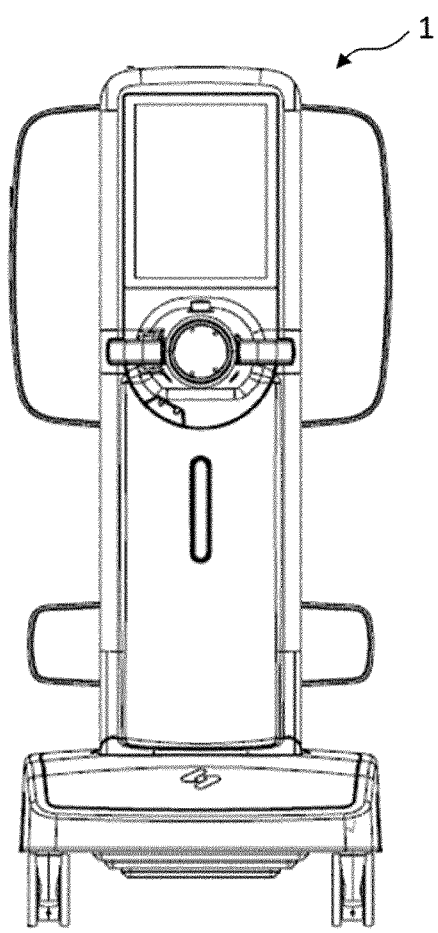
FIG. 3: a front view of a robot device according to one embodiment of the invention without articulated robotic arm.

The upper part 21 of the frame 2 comprises a robotic arm 6 mounting bracket. FIG. 2 shows an example of a robotic arm 6 of the invention that is plugged into a mounting bracket 24.

The mounting bracket 24 comprises a cavity for receiving a proximal end of the robotic arm 6. According to different attachment modes, the robotic arm 6 can be plugged in, clipped or screwed into the receiving cavity. According to different embodiments, the mounting bracket 24 comprises a clamping means and a locking means 241 of the robotic arm 6. The clamping means makes it possible to obtain solidarity between the robotic arm 6 and the frame 21 by limiting the play between the parts. It also allows the robotic arm 6 to be held better by the frame 2. The locking means 241 makes it possible to secure the fastening in order to prevent an accidental separation of the robotic arm 6 from the frame 2.

The mounting bracket 24 is preferentially made integral along at least one axis with the frame 2. According to one embodiment, the robotic arm 6 is fastened to the frame 2 along an axis substantially perpendicular to the plane of the upper part 21. When the main plane of the upper part is vertical, the robotic arm 6 is held along a horizontal axis at the level of the mounting bracket 24.

The robotic arm 6 is an arm comprising a plurality of portions, each being articulated relative to another according to at least one degree of freedom. The proximal portion 60 is the portion intended to fit into the mounting bracket 24. The distal portion 65 is the portion intended to hold a distal operator device 8. The latter distal operator device 8 is intended to navigate close to a patient's skin to allow interaction, such as taking a photo, emission of a laser beam, sensory contact.

According to one embodiment, the mounting bracket 24 comprises a pivot link making it possible to orient the main axis of the receiving cavity or the proximal axis of the robotic arm 6, i.e. the proximal portion 60 thereof. According to one embodiment, the axis of the distal portion 60 of the robotic arm 6 can therefore be arranged perpendicular to the plane of the upper part 21 upon its introduction, then it can be tilted by an action on the mounting bracket 24. To this end, the mounting bracket 24 can be made moveable according to a degree of freedom. In this case, it may for example comprise an orientation handle and a device for locking the orientation of the robotic arm 6. In another case, the adjustment of the orientation of the base of the mounting bracket 24 of the robot arm 6 is motorized and can be controlled from the interface or a button. Thus, after unlocking the orientation, an operator is able to orient the robotic arm 6 along a desired inclination and lock the new orientation of the axis of the distal portion of the robotic arm 6 held in the mounting bracket 24. According to one example, the pivot connection is a ball joint connection, for example, limited in its degrees of freedom to corner portions. Such a ball joint connection allows, for example, the axis of the proximal portion to be oriented in the plane $P_1(0, y_1, x_1)$ or in the plane $P_2(0, y_1, z_1)$ of the coordinate system $R_1$ shown in FIG. 1.

Figure 12:
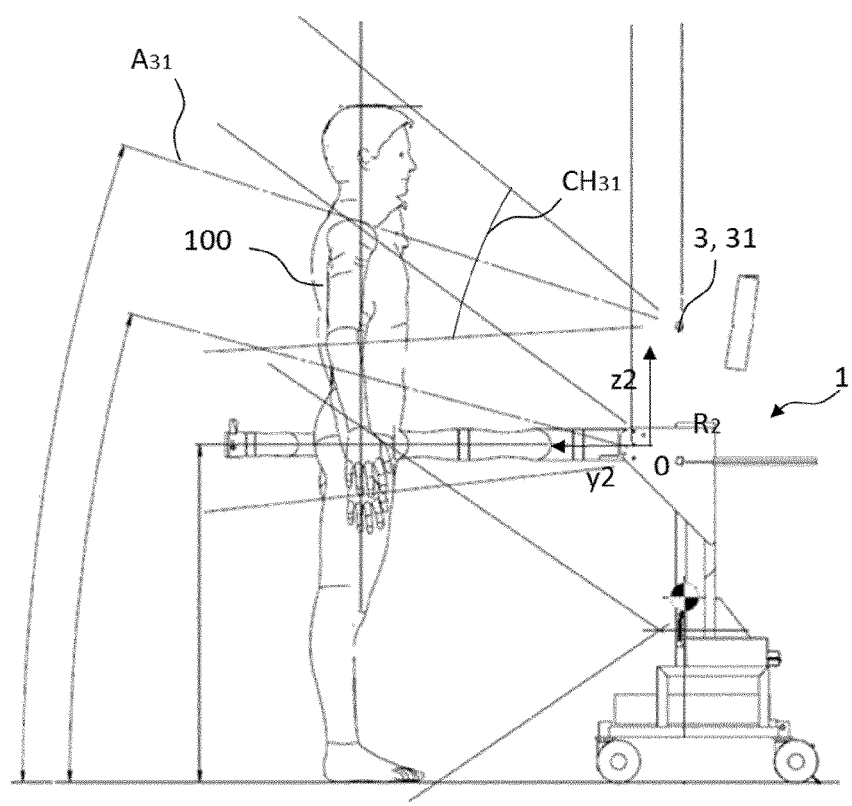
FIG. 12: an exemplary arrangement of the robot device of the invention making it possible to go all over the surface of a body of a patient in a standing position.
Figure 13:
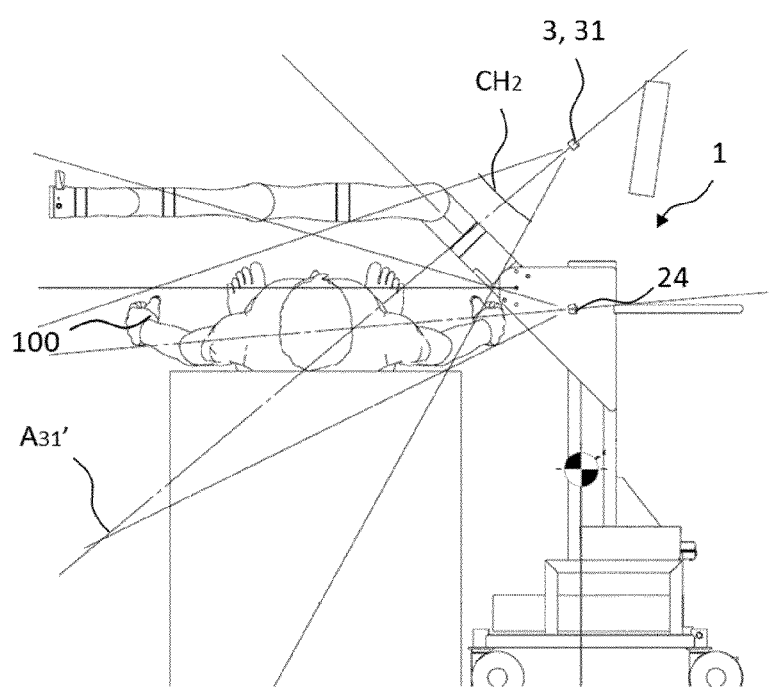
FIG. 13: an exemplary arrangement of the robot device of the invention making it possible to go all over the surface of a body of a patient in a lying down position.

FIGS. 12 and 13 show two different positions of the robotic arm 6 which is attached to the mounting bracket 24. The mounting bracket 24 is shown here according to another example. The proximal portion of the robot arm 6 has changed orientation between FIG. 12 and FIG. 13 by around 45°. In this example, the mounting bracket 24 comprises a pivot link allowing the proximal part of the robot arm 6 to be oriented around an axis comprised in the horizontal plane.

Image Acquisition System

The robot device 1 of the invention comprises a plurality of optical devices 3. According to the example of FIG. 1, 6 optical devices are arranged on the upper part of the frame 2. According to one embodiment, the optical devices 3 are arranged in a same plane and are by default oriented along a same axis. An interest of the invention is to configure a robot device 1 of the invention that can provide a wide field of view in order to acquire images of a human body in a standing or lying down position.

To this end, different configurations are possible according to different alternative embodiments which can be combined with each other according to the number of optical devices 3 that it is wished to use.

A first alternative consists in spacing the optical devices 3 a certain distance apart to increase the field of view in width $Fov_1$, in the plane $P_1(0, y_1, x_1)$ in FIG. 1. The different optical devices 3 are preferably spaced within the width of a distance comprised between 10 cm and 2 m. More specifically, a distance between two optical devices 3 arranged on a same horizontal axis may be between 30 cm and 150 cm. In order to obtain a robot device 1 that is as compact as possible and can, for example, be displaced from one room to another, a distance between two optical devices 3 arranged on a same horizontal axis may be between 30 cm and 60 cm. This distance between two optical devices 3 allows the field of view to be increased horizontally to acquire the image of a patient having his arms detached from his body extending along a horizontal axis.

A second alternative consists in spacing the optical devices a certain distance apart to increase the field of view in height $Fov_2$, in the plane $P_2(0, y_1, z_1)$ in FIG. 1. The different optical devices 3 are preferentially spaced apart within the height of a distance comprised between 10 cm and 2 m. More specifically, a distance between two optical devices arranged on a same vertical axis may be comprised between 30 cm and 150 cm. According to a smaller range offering a better compactness of the robot device 1, the distance separating two optical devices 3 vertically is between 30 and 60 cm. This distance between two optical devices 3 allows the field of view to be increased vertically to acquire the image of a patent from head to foot while he is positioned standing.

FIG. 12 shows an example in which the device 1 is represented in a given position where the vertical field of view $CH_{31}$ of the optical device 31 is approximately 45°.

A "virtual field of view" designates a combination or union of real fields of view of several optical devices 3. The virtual field of view corresponds to the association of several actual fields of view considered from different positions. Thus, the virtual field of view is the field of view of the optical system 3' considering a virtual source from which the virtual field of view could be considered.

A third alternative embodiment consists in positioning rows of optical devices 3 substantially aligned along a vertical or horizontal axis on the robot device 1. Thus, in FIG. 1, the optical devices 32, 31 and 35 are substantially aligned vertically, the optical devices 33, 334 and 36 are substantially aligned vertically, the optical devices 32, 33 are substantially aligned horizontally, the optical devices 34, 31 are substantially aligned horizontally, the optical devices 36, 35 are substantially aligned horizontally.

This configuration makes it possible to offer an acquisition coverage making it possible to acquire images of a patient standing or lying down on a table while offering a reduced bulk.

According to one embodiment, several robot devices 1 of the invention can be combined to acquire a larger field of view or to obtain a complete scan of a patient, of which his front face and his back face without him needing to turn round. A calibration between the robot devices 1 is then carried out to represent the point clouds generated from the images acquired in the same frame of reference.

Figure 6:
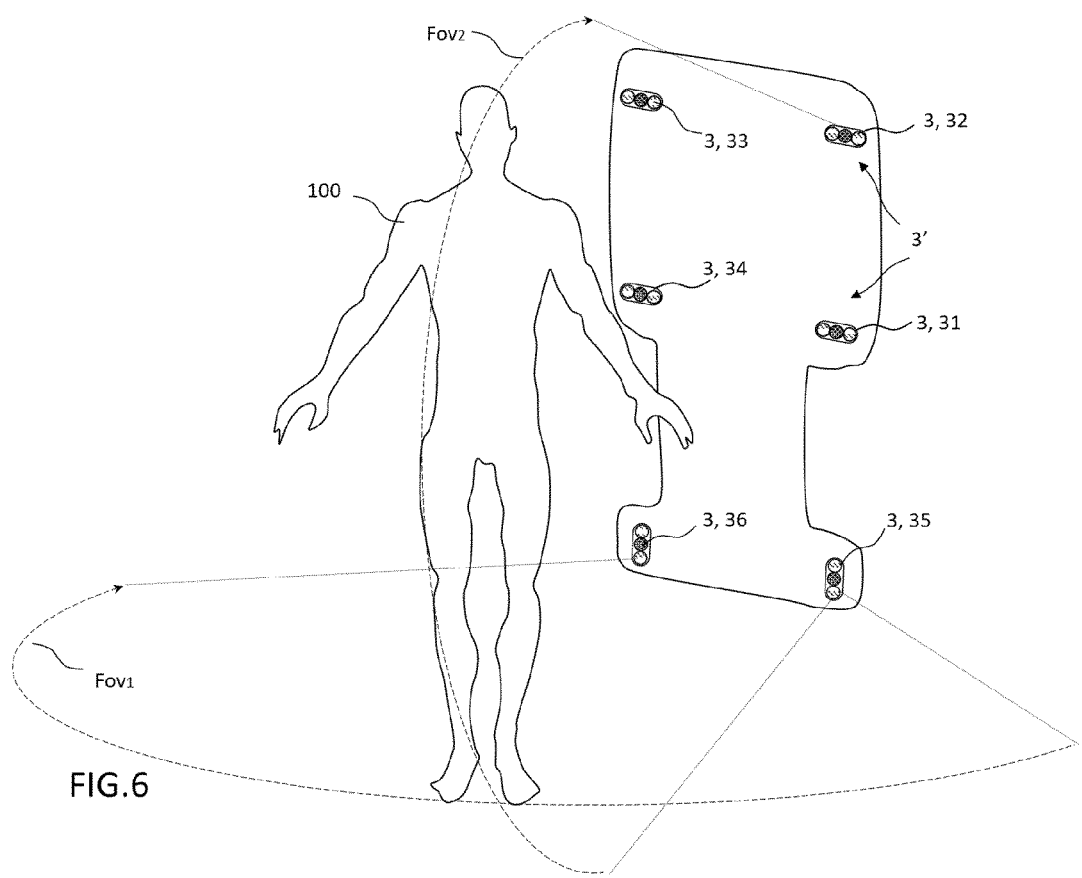
FIG. 6: an exemplary arrangement of the acquisition system allowing a field of view to be obtained to acquire the surface of a body of a standing patient.

FIG. 6 shows an example of the positioning of a patient 100 standing in front of the robot device 1 of which only the optical system 3' is shown. In this figure, the virtual fields of view in width and height $FoV_1$ and $FoV_2$ of the optical system 3' are shown. The virtual fields of view are constructed by associating the actual fields of view of each optical device 31, 32, 33, 34, 35, 36. The distribution over a given surface extends the virtual field of view of the optical system 3' to cover the entire body surface of a human 100. An advantage of arranging a plurality of optical devices 3 distant from each other by a given distance is to increase the overall field of view of the optical system 3' while retaining optics with a depth of field making it possible to generate a sufficiently precise depth map.

Another advantage is to reduce the occlusion caused by displacements of the robot arm 6 in front of the optical system 3'. Thus, by multiplying the optical devices 3, the generation of the overall point cloud, from different point clouds generated from different points of view, can compensate for the effects of occlusion and masking of the patient's body 100 by the robot arm 6.

Optical Device

Each optical device 3 is configured to generate a 3D image. For the purpose of the present invention, a 3D image can be understood as a set of images of a same subject, at least two images, for generating depth information of said subject. According to one example, the 3D image can be a stereoscopic image, i.e. a pair of images, such as two so-called left and right views, taken by two optical sensors taking a same scene from two slightly distant points of view. The spectrum of such an image may be in the visible or the infrared. In this case, a 3D image can be a pair of color or infrared images. According to another example, a 3D image can also be understood as an image that is directly associated with a depth map, according to another example, a 3D image can be understood as a point cloud representing a sampling of a three-dimensional surface obtained from acquired images of a subject. The 3D image may also comprise other information, in addition to points, such as color information. According to one embodiment, the 3D image comprises a 2D image and depth information estimated by a depth estimation algorithm. According to one embodiment, the 3D image comprises a 2D image and a three-dimensional mesh calculated according to the method of the invention.

More generally, a 3D image designates: a 2D image with which is combined digital information making it possible to construct a three-dimensional representation of a surface in space. This digital information may be a second image, a depth map, or any other calculated data making it possible to construct a point cloud in space from a 2D image.

According to one embodiment, each optical device 3 comprises a pair of cameras making it possible to generate a depth map of the acquired image. According to one example, the cameras are infrared cameras. Infrared cameras offer resolutions that enable a depth map to be drawn, the accuracy of which makes it possible to reproduce differences in reliefs on the surface of a patient's body located at a distance between 30 cm and 3 m, or even 4 m, from the robot device 1.

According to one method, 2D images acquired from the same object from two points of view of which the arrangement is known may be combined using known techniques to obtain a so-called depth or distance map.

According to one embodiment, each optical device 3 comprises 3 cameras, of which a pair of infrared cameras and a color camera.

According to one example, the acquisition devices may comprise a pair of 3D color infrared cameras and at least one infrared projector. According to one embodiment, the optical device 3 comprises a laser infrared projector making it possible to project an image comprising patterns, notably on the surface of a human body. The projected pattern is then acquired by the pair of infrared cameras in order to reconstruct a depth map in real time by stereoscopy.

According to another example, the acquisition devices may comprise a pair of color cameras configured to make passive stereo in order to generate 3D images.

According to another example, the acquisition devices may comprise a color camera and a light projector projecting structured light patterns.

The acquired images can then be processed to analyze the distortion of the projected pattern. This technique makes it possible to obtain an additional datum and makes it possible to improve the 3D reconstruction. In particular, detecting a distortion of a projected pattern makes it possible to improve the accuracy of the discrepancy map between two images used to generate the depth map. Further, the projector makes it possible to reduce noise when constructing the point cloud to generate the first graph $G_1$.

According to one embodiment, the patterns of the image are regular patterns for example representing a regular shape. According to another embodiment, the patterns are generated randomly.

According to alternative embodiments, other technologies may be implemented in the invention to reconstruct a depth map for example from time-of-flight camera. In the latter case, the 3D camera can, for example, be replaced by a time-of-flight camera, also known as ToF. In this case, it is a visible or infrared light or laser beam coupled with a camera or photosensitive receiver making it possible to measure the time-of-flight of different beams fired in the space and hence to reconstruct a 3D mapping.

Other techniques for constructing a depth map may be used, such as a laser transceiver device. The reflection of the laser beam is used to generate a datum on the geometry of the reflection surface. Another technique may be based on an ultrasonic transceiver. An example of a system that could be implemented is the LIDAR type system.

Calibration

An inter-camera calibration, called "stereoscopic calibration", can be performed, for example, between the two cameras of a same optical device 3 to perform a 3D reconstruction of a subject. The calibration aims to calculate a transformation between two images acquired by each camera. This calibration makes it possible to ensure the transformations between the coordinate systems of the different cameras/projectors of a same optical system 3', for example, the transformations between the 3 cameras/projector 331, 332, 333 shown in FIG. 10 of the optical device 33.

Finally, this calibration makes it possible to ensure the transformations between one optical device 3 and another optical device 3. The calibration may comprise the definition of a reference camera of an optical device 3 so that the transformations are carried out by chain to any coordinate system of the device in which the reference camera is defined.

A calibration of the robot arm 6 makes it possible to know the transformation between the common coordinate system of all the optical devices, for example chosen arbitrarily from all of the coordinate systems of each optical device 3, and that of the robot arm 6 which can be defined at the level of the origin of the arm.

The following coordinate systems are defined: $R_0$: global frame of reference in which the robot device 1 evolves $R_1$: frame of reference linked to the robot device 1 at a point on the frame;

$R_2$: frame of reference linked to the fixed part of the robot arm 6 vis-à-vis the frame of the robot device 1;

$R_3$: frame of reference linked to the head of the robot arm 6;

$R_{31}$: frame of reference linked to the optical device 31;
$R_{32}$: frame of reference linked to the optical device 32;
$R_{33}$: frame of reference linked to the optical device 33;
$R_{34}$: frame of reference linked to the optical device 34;
$R_{35}$: frame of reference linked to the optical device 35,
$R_{36}$: frame of reference linked to the optical device 36.

The method of the invention therefore makes it possible to calibrate the robotic arm 6 with respect to the acquisition system 3' or the frame 2 and thus to perform the transformations of the images in the frames of reference $R_3 \rightarrow R_1$. When a frame of reference $R_3$ is associated with the head 8 of the robotic arm 6, a transformation of $R_3 \rightarrow R_1$ is known on account of the articulation kinematic of each part of the robot arm 6 is known by a calculator and a memory of the system controlling said robot arm 6.

According to one example, an optical device 3 is determined as a reference. One advantage is, on the one hand, to calibrate all cameras of the optical system 3' in relation to a single optical device 3 and, on the other hand, to calibrate the position of the robot arm 6 in relation to this same optical device 3. Thus, this calibration with respect to a single camera or a single reference optical device 3 makes it possible to ensure that the displacements of the robot arm 6 are indeed referenced in a coordinates system common to the optical system 3'.

The calculation of transformations can also be performed by an iterative alignment process of the different point clouds generated by the different optical systems. Such an algorithm is called "iterative closest points" in English terminology.

According to another embodiment, calibration may also be performed by studying the transformation there is between a color image pair.

The calibration can be performed from a reference pattern. Typically, a projection of an image can be used. This can be a projection of a pattern by the projector in combination with an optical device 3. An exemplary embodiment comprises the projection of a grid of which the distortions acquired by each camera make it possible to generate a corrective factor to compensate the position or orientation of said camera with respect to another camera, or respectively an optical device 3 with respect to another optical device 3.

This calibration ensures that a point cloud calculated by one optical device 3 corroborates with another point cloud calculated by another optical device 3.

Orientable

Figure 10:
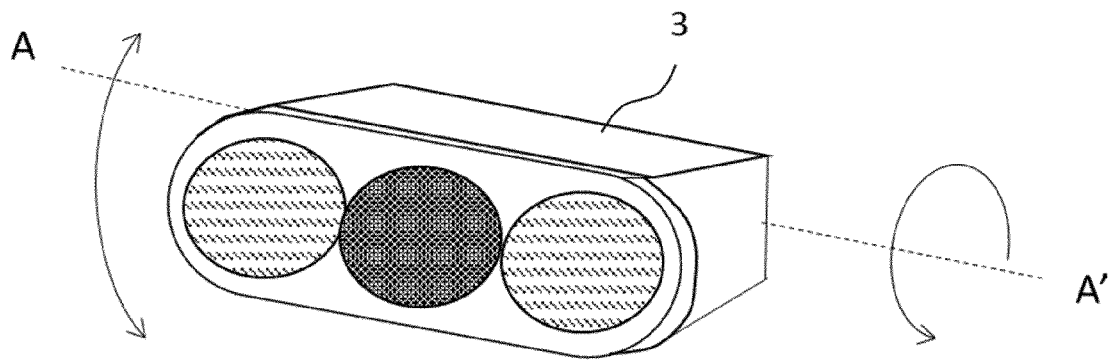
FIG. 10: an example of an orientable optical device according to the invention.

According to one embodiment, at least one optical device 3 is orientable along an A-A' axis shown in FIG. 10. The pivoting of the optical device 3 makes it possible to obtain modulable field of view configurations. For example, an orientation of one or more optical devices 3 makes it possible to adapt a field of view, for example, to a specific case such as a small patient or to adapt the image to a position of a patient lying down or standing. The pivoting can be configured in an angle range of [−60°; +60°] with respect to a default axis comprised in the horizontal plane. According to one embodiment, at least two degrees of freedom can be controlled to orient each optical device or at least a portion of the optical devices. According to one embodiment, 3 rotations per ball joint link are controllable.

FIGS. 12 and 13 show the optical device 31 in two different orientations that are adapted to the position of the patient 100. In FIG. 12, the optical device 31 is oriented to cover a portion of a patient's torso in a standing position. In FIG. 13, the optical device 31 is oriented to cover a portion of a patient's torso in a lying down position. The pivoting between the two orientations of the device 31, i.e. between the two straight lines $A_{31}$ and $A_{31}'$ may correspond to an angle of +20°/horizontal axis in FIG. 12 and −40°/horizontal axis in FIG. 13.

According to an exemplary embodiment, the pivoting(s) of one or more optical devices 3 can be controlled from a console or a user interface of said robot device 1.

According to one example, at least one optical device 3 is removable and can be replaced by a different optical device 3. One benefit is to change the field of view of the optical device 3.

According to another example, the optical device 3 is removable to be clipped in another position. Thus, in this configuration, each optical device 3 can be inserted in a housing allowing different orientations to be offered.

Figure 9:
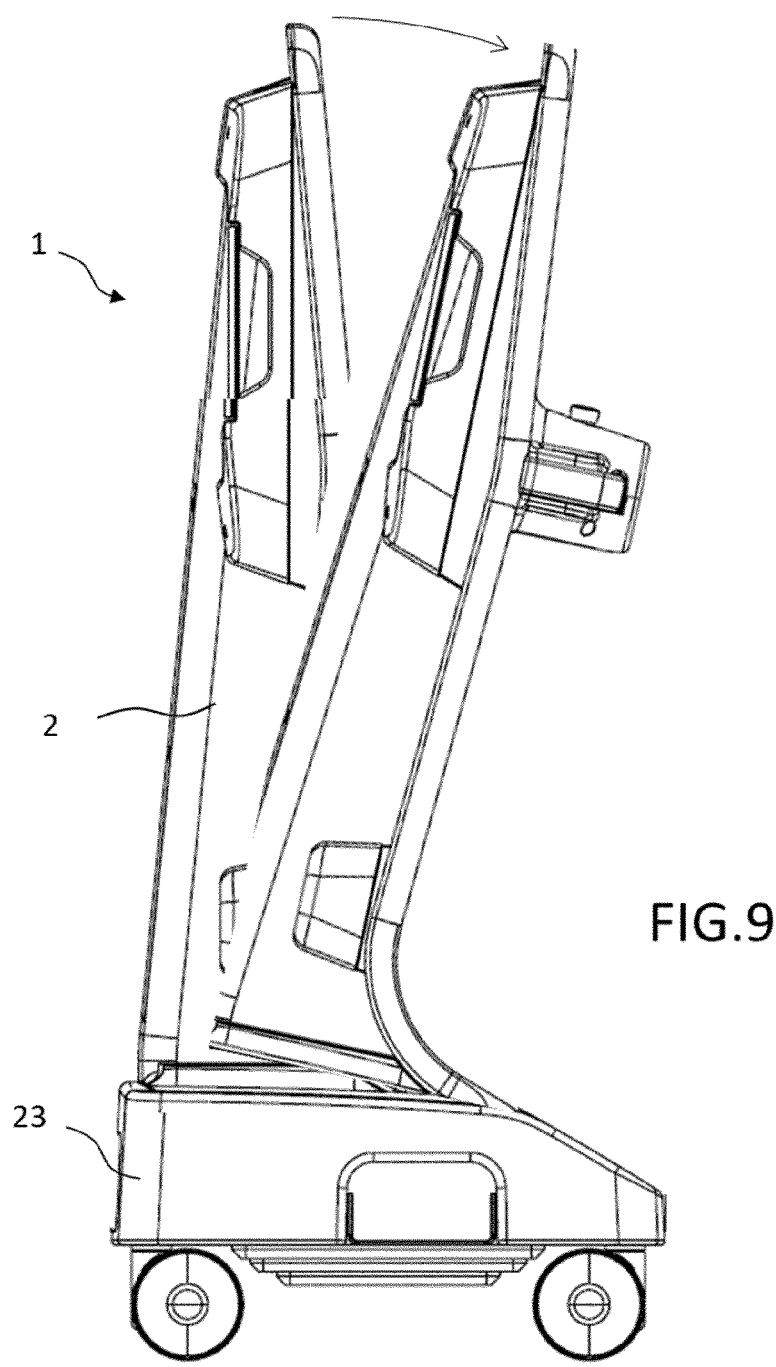
FIG. 9: an example of a device of the invention tilting to adapt a field of view to a given situation.

According to an exemplary embodiment, in order to adjust the field of view of the acquisition system 3' to a positioning of a patient, the frame 2 may comprise a moveable part, for example in rotation. FIG. 9 shows an example of a pivot link arranged between the frame 2 and the base 23 which allows the frame 2 to be pivoted by a given angle.

According to another example, fins 22 can be made orientable, either along a vertical rotation axis or along a horizontal rotation axis.

Electronic Device

The robot device 1 of the invention comprises an electronic device (not represented) comprising a calculating entity which comprises at least one calculator which may be an electronic component provided with a processor. The electronic device further comprises a memory for storing configuration parameters of the robot device 1, the calibration parameters of the robot device 1 and notably the optics of the optical system 3', the instructions necessary to run the software operating to calculate the trajectories of the robot arm, the surfaces of a patient's body, the configuration and parameterization data of sensors, transmitters or any other equipment controlled by the robot arm 6, data such as those making it possible to run the network of neurons used to reconstruct the surface of a patient's body from optical data such as an image, a depth map or a point cloud. The latter neural network data may comprise network coefficients, classifier data, regression function data.

The electronic device may be a single component or, instead in a second embodiment, it may comprise different components which are associated with different elements of the robot device 1, such as the robot arm 6, the optical system 3', the screen 4.

A first purpose of the electronic device is to generate a surface of a patient's body in real time from images acquired by the optical system 3'.

Point Cloud

From the depth map, the invention makes it possible to generate a point cloud in the space representing a mesh of the surface of a human body. Each point in the point cloud can be associated with a three-dimensional spatial coordinate of a frame of reference linked to the robot device 1. The points then constitute a first graph $G_1$. According to an example, the points of the first graph $G_1$ obtained are not oriented and not connected. In its simplest form, the graph $G_1$ is a list of unordered points whose coordinates are referenced in space, for example in a frame of reference of the space in which the robot device 1 is located or a frame of reference associated with the robot device 1. The points are then defined independently of each other. In its simplest form, the graph $G_1$ is therefore a point cloud.

According to one embodiment, the method of the invention makes it possible to retrieve a point cloud derived from the acquired images and to transfer it for example to a graphic processor such as a GPU, GPU denoting in English terminology "Graphic Processing Unit".

The images can be processed so as to extract an acquisition perimeter limiting the area to be processed. For this purpose, a template or segmentation mask, optionally obtained using a neural network, can be used to avoid taking into consideration points outside an area of interest defined by the surface of the body.

The acquisition of images and the coverage of the entire surface to be treated generates a depth map of the entire body of a patient. The depth map comprises a grid of points/pixels whose intensity corresponds to the relative distance from the camera.

According to another example, no surface is treated at this stage of the method. The distances between points are generated independently from a shape recognition such as a body shell.

According to an example, the number of points generated per surface unit is configurable according to a desired resolution of the point cloud. The acquisition can be configured to increase the spatial resolution of the point clouds by increasing image resolution. It can also be configured to increase the temporal resolution by increasing the number of images collected per unit of time.

According to one embodiment, each optical device 3 calculates a point cloud from the acquired images. Each optical device 3 comprises a set of points. According to the example of FIG. 1, at each acquisition the optical system 3' activates all of the optical devices 3 so that:
  the optical device 31 generates a set $ENS_{31}$ of points of the point cloud;
  the optical device 32 generates a set $ENS_{32}$ of points of the point cloud;
  the optical device 33 generates a set $ENS_{33}$ of points of the point cloud;
  the optical device 34 generates a set $ENS_{34}$ of points of the point cloud;
  the optical device 35 generates a set $ENS_{35}$ of points of the point cloud,
  the optical device 36 generates a set $ENS_{36}$ of points of the point cloud.

The electronic device comprises calculation means for generating an overall point cloud, noted $ENS_G$, comprising all points of the different sets generated $ENS_{31}$, $ENS_{32}$, $ENS_{33}$, $ENS_{34}$, $ENS_{35}$, $ENS_{36}$. One benefit is to obtain as complete a point cloud as possible representative of a patient's body while maintaining a compact system.

The electronic device allows the following operations to be performed:
  application of a transfer function based on a calibration configuration of the different optical devices 3 with respect to a reference point of the robot device 1;
  correlation between the different sets of points in order to determine a common subset of points and a subset of points not shared by the different point clouds;
  optionally, check for calibration errors of an optical device 3;
  determination of an overall point cloud comprising all of the points of the different sets of points generated by each optical device 3.

Point Cloud Processing and Shape Descriptor Calculation

The robot device 1 of the invention comprises a calculator for reconstituting the surface of a human body faithfully to that of a patient from the images acquired for calculating local shape descriptors. According to one embodiment, a connected graph is obtained from the mesh of points. The method consists in associating with each point of the connected graph attributes derived from calculations made on the adjacent matrix of the connected graph. This corresponds to the calculation of functions applied to each point, of which its coordinates, and their neighborhood in order to generate shape descriptors, or shape coefficients.

An advantage of shape descriptors is to characterize a local topology of the surface at a point in the first graph $G_1$. When a patient's body moves or changes over time, the body surface is considered as a deformable object of which the transformations are non-isometric. The shape descriptors make it possible to generate at each point specific characteristics that it is possible to recover by the method of the invention after a deformation.

Using a Trained Neural Network

The device of the invention comprises an electronic component comprising at least one memory and a calculator for calculating a human body model from a trained neural network. Implementation of the trained neural network can be performed so that it processes, at the input, vectors comprising the coordinates of each point of the point cloud and previously calculated attributes associated with said points, and, at the output of the neural network, produces a new connected point cloud, such as a connected graph, which represents the surface of the patient's body whose images have been acquired. The generated body surface is also called a parameterized body model MOD_P in so far as the parameterization corresponds to that of the patient and it is generated from the acquired images. According to another embodiment, the body model is non-parametric.

According to one embodiment, the training of such a network can be performed from a parametric model of the human body defined by parameters such as parameters of shapes and rotations of articulations.

Alternatively, at the exit of the trained neural network, it can be calculated by a regression of the parameters of a parametric model of a human body to generate a body model corresponding to that of the patient. The electronic device is then able to calculate the point cloud corresponding to the parametric model parameterized with the parameters derived from the neural network regression.

Another alternative is to use a trained neural network making it possible to directly generate a connected graph G corresponding to the patient's measured point cloud. This solution makes it possible to avoid using a parametric model of the body at the output.

Thus, the surface of a human body can be calculated in real time from an image acquisition by the robot device 1 and a trained neural network.

One benefit of a real time calculation of a modeled surface of the patient's body is to anticipate, for example, the movements of said patient to take into account movements, for example, from the breathing of the patient 1.

The advantage of the method of the invention is to be able to generate a new modeled surface in less than 30 ms. These response times make it possible, in particular, to control the movements of a robot arm 6 with a sufficient speed to anticipate collisions or sudden movements in order to clear as quickly as possible. The configuration of an acquisition by a camera may be for example from 10 to 90 fps.

According to one embodiment, a first three-dimensional image may be generated by the electronic device 3 from all the images acquired by the optical system 3' so as to obtain an overall view of the body of a patient.

Guiding of the Robot Arm

A second objective of the electronic device is to generate guiding instructions in real time to enslave the movements of the robot arm 6 according to a trajectory updated as a function, on the one hand, of a predefined planning strategy and, on the other hand, of data recalculated in real time corresponding to the surface of the patient's body MOD_P. The data of the patient's body MOD_P are updated in real time, because the patient may accidentally move or change position at the request of a physician, or breathe while the robot arm is moving on or near the rib cage, etc.

The robot arm 6 is guided by a movement controller GEN_TRAJ which takes into account different constraints to enslave the robot arm 6. Notably, the controller CTRL can take into account an instruction from a collision detection module to adapt the robot arm's travel in real time. Finally, the controller CTRL takes into consideration data coming from the head of the robot 6 by means of a module CNTR_8, for example when a detection of a singular image imposes a particular manipulation of the robot, such as a change of travel, a stop of the travel, etc.

Figure 11:
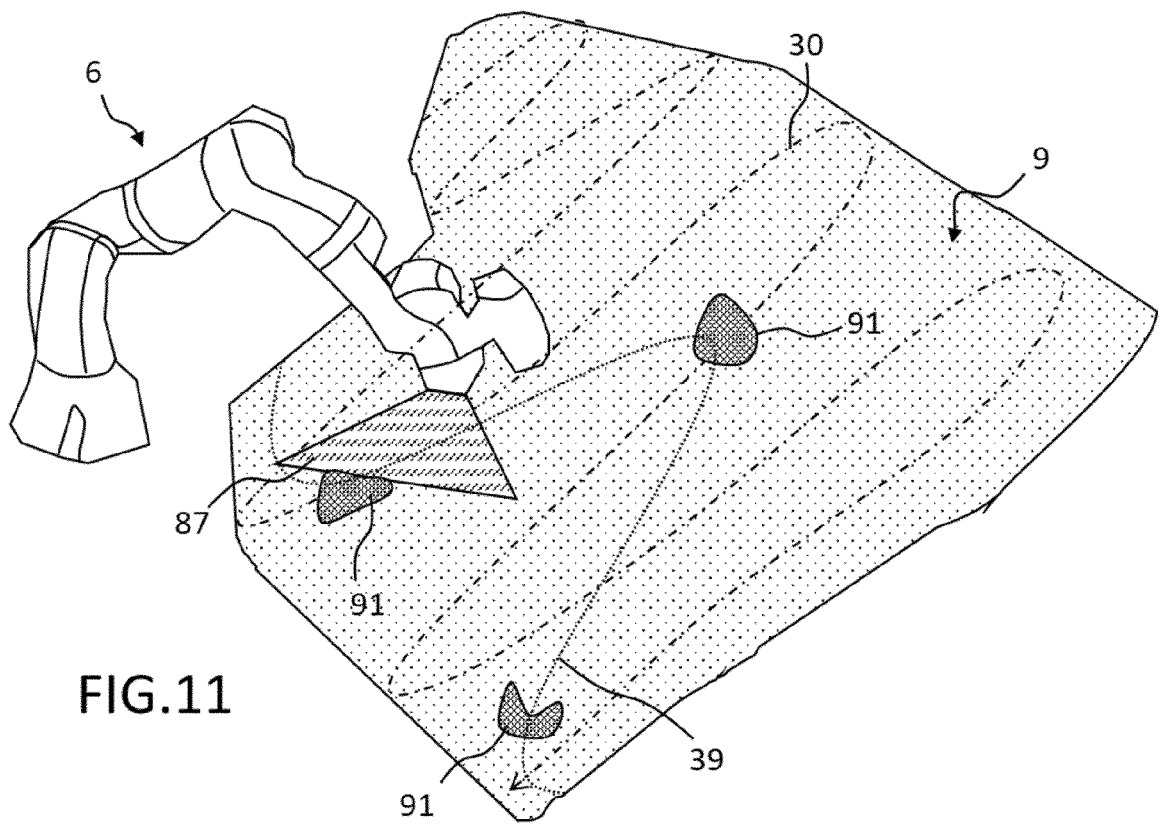
FIG. 11: an example of a planned trajectory on the surface of the body of a patient that is recalculated in real time to enslave the displacements of a robot arm of the invention.

A robot arm 6 is guided from a treatment trajectory, noted 30 in FIG. 11, established within a defined area 9 of the surface thus modeled and recalculated in real time.

The trajectory 30 can be obtained from a scanning strategy of the robot arm 6. According to an example, the generated trajectory 30 is obtained thanks to a planning module PLAN_TRAJ which can be accessed, for example, from a user interface 4 or any other user interface remote from the robot device 1.

From the trajectory 30, associated trajectories can be calculated to guide the robot arm 6. This may be the trajectory of the distal operator device 8 for example when a certain distance between the distal operator device 8 and the skin surface of a patient must be respected.

In the example in FIG. 11, three dermatological singularities 91 are represented on a portion 9 of skin of a patient 1. For example, it could be a scar, a melanoma, a beauty spot, or any other singularity of the skin surface. When the optical field 87 of the distal operator device 8 intercepts a singularity 91, the robot arm 6 can be configured to stop its travel or activate another equipment such as an optic to acquire images of the singularities which are dynamically analyzed in real time to enslave the robot arm 6 or subsequently to establish a diagnosis, for example.

Figure 5:
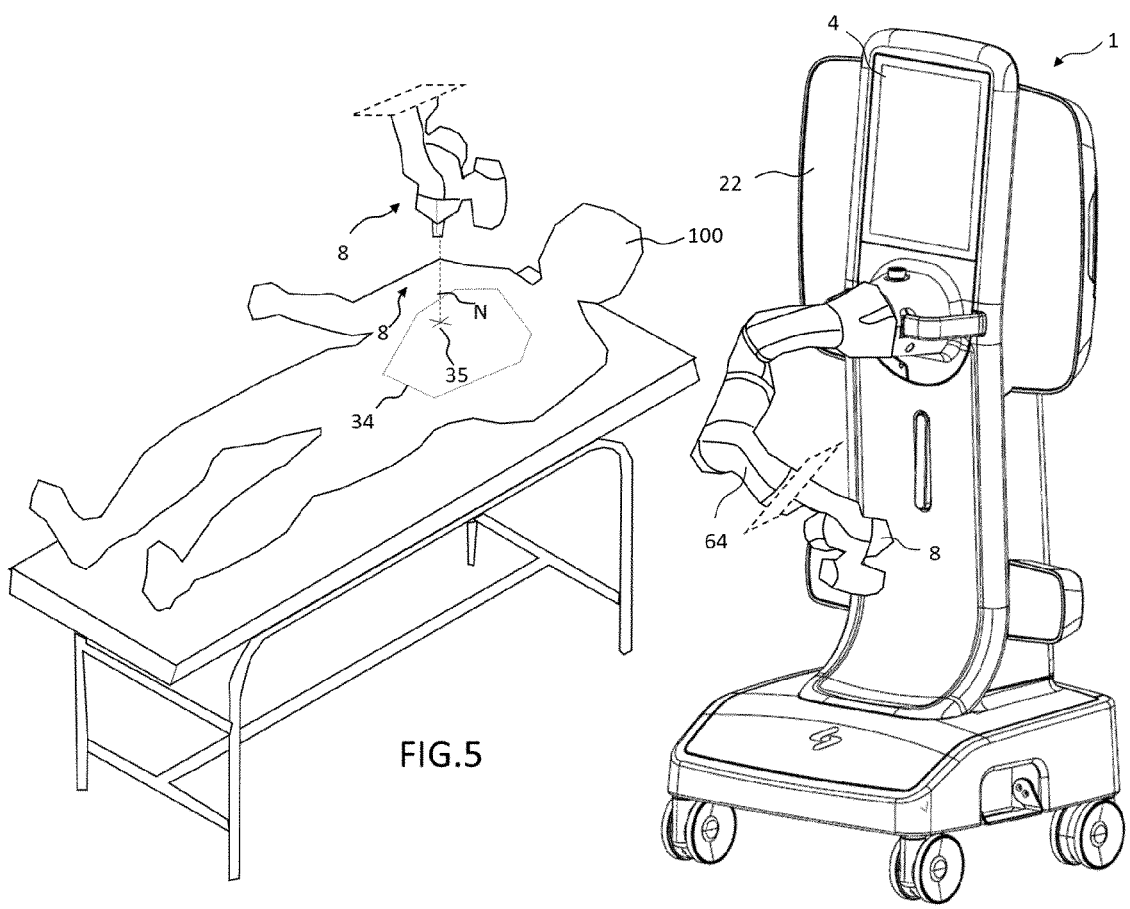
FIG. 5: an exemplary arrangement of a robot device of one embodiment of the invention alongside an intervention table on which a patient is placed.

According to an example, the orientation between the axis of the distal operator device 8 and the skin surface is determined by default at 90°. This angle corresponds to the situation where the main axis of a sensor or transmitter of the distal operator device 8 of the robot arm 6 is merged with the normal N at the target point 35 of the surface of the body under consideration. FIG. 5 shows a view in which the distal part 65 of the robot arm 6 is illustrated above a lying down patient.

The end of the distal operator device 8 is positioned at a given distance from the aiming point 35 located on the surface of the modeled body located, for example, on the generated trajectory 30.

According to another embodiment, the end may also be applied against the patient's skin. The controller is configured to regulate the force applied to the patient's skin, for example to place a Dermatoscope, or an ultrasonic probe.

The robot device 1 of the invention further comprises a calculation of a new kinematic of the robot arm 6 enslaved to the definition of the new trajectory 30. One advantage is to obtain good guiding performance in real time. Taking into consideration a body model simplifies the guiding calculations. The robot arm 6 can be enslaved quickly and thus it makes it possible to limit cases of collisions or sudden movements of a patient.

Figure 4:
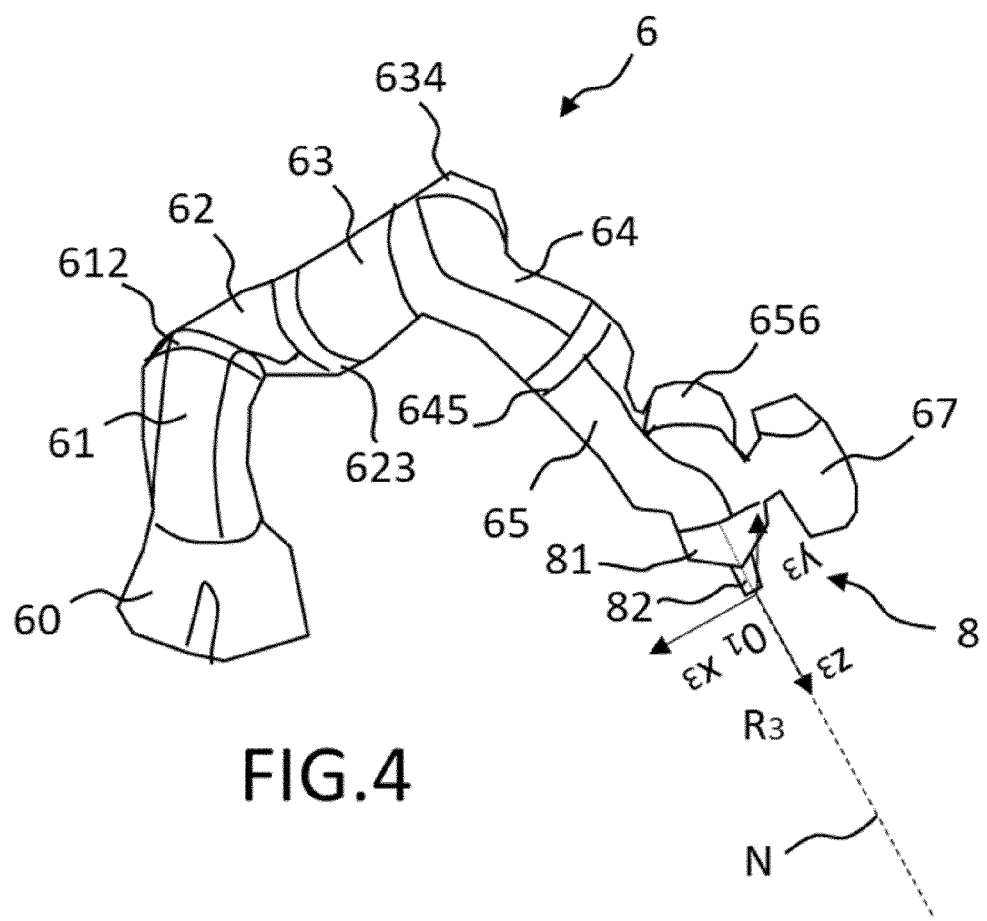
FIG. 4: a robotic arm suited to be attached to a robot device according to an embodiment of the invention.

The distal operator device 8 may be linked to a coordinate system noted $R_3$ ($O_3$, $x_3$, $y_3$, $z_3$) shown in FIG. 4. The position of the distal operator device 8 of the robot arm 6 can be easily identified in the coordinate system $R_2$ ($O_2$, $x_2$, $y_2$, $z_2$) with knowledge of the kinematics animating the different parts of the robot arm 6. One benefit is to reference the images acquired by the distal operator device 8 for example in the coordinate system $R_1$ (O, $x_1$, $y_1$, $z_1$) or $R_0$ (O, $x_1$, $y_0$, $z_0$).

Thus, the electronic device of the robot device 1 is configured to deliver guiding instructions in real time to the motor element of the robot arm that it is able to determine the kinematics of each part of the robot arm 6.

Robot Arm

According to one embodiment, the robot arm 6 comprises a set of branches 61, 62, 63, 64, 65 articulated by means of pivot articulations 612, 623, 634, 645, 656. In this case, the robot arm 6 comprises 5 branches articulated from pivot links. According to an alternative embodiment, it comprises 6 articulated branches and according to other alternative embodiments, it may comprise 7, 8 or 9 articulated branches. Indeed, in this embodiment, each articulation is capable of performing at least one rotation between two adjacent branches.

According to one embodiment, each branch of the robot arm 6 comprises a force sensor. One advantage is to prevent a sudden collision. When a contact is established between a branch of the robot arm 6 and an object, the movement of the robot arm can be automatically stopped or its guiding changed so that it changes its trajectory. Another advantage is to calculate the force applied to the patient when the distal operator is in contact with his skin.

According to one embodiment, a step of calibration of the robot arm 6 is performed prior to the method of the invention. The calibration may comprise the relative positioning of the robot arm 6 in the coordinate system $R_2$ vis-à-vis the coordinate system $R_1$ or any coordinate system $R_{31}$, $R_{32}$, $R_{33}$, $R_{34}$, $R_{35}$, $R_{36}$ associated with an optical device 31, 32, 33, 34, 35, 36 of the optical system 3' as well as its initial position.

Distal Operator Device

According to one embodiment, the robot arm 6 comprises a distal operator device 8 advantageously arranged at the end of the robot arm 6. According to one example, the distal operator device 8 comprises at least one sensor and/or at least one transmitter. The distal operator device 8 is also called the "head" of the robot arm 6.

Figure 7:
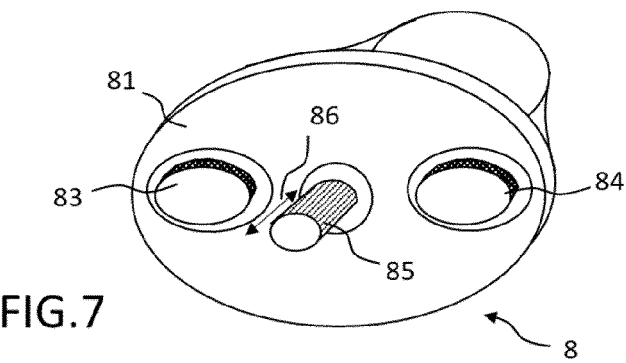
FIG. 7: a first example of the head of a robotic arm of the robot device of the invention.

According to the embodiments, a distal optical system 83, 84 may be arranged at the end of this distal operator device as in the case of FIG. 7. One benefit of the configuration of FIG. 7 is to configure a robot arm 6 for image capturing dermatological applications.

In the example of FIG. 7, the robot arm 6 is provided with one or more optical sensors 67 to acquire local images of the surface of the skin. One benefit of taking local images at the head of the robot arm 6 is the possibility of reconstructing a surface of the body "colored", i.e. in which the images taken are integrated into the parametrized body model MOD_P generated by the method of the invention. To this end, the optical device 3 located at the end of the robot arm 83, 84 may preferentially comprise two optics so as to reconstruct a depth map associated with the images acquired simultaneously by the two optics. The images can then be indexed to the surface of the parameterized body. It is understood, for example, that the images of singularities 91 of FIG. 11 can be recorded and associated with a position of a body model MOD_P of a patient. Thus, several months later, during a check, the robot device 1 is able to generate a trajectory 39 passing through a set of points associated with singularities to check the evolution of the images of the singularities with respect to reference images.

According to one embodiment, the distal operator device 8 comprises two local optics 83, 84 for taking images of the body surface and a millimetric 85 or bidirectional removable microscopic optic in a longitudinal direction 86. One benefit is to generate images with millimetric resolution comprising a resolution for dermatological applications, for example for diagnostic applications.

The second distal optical device 85 therefore makes it possible to take an image of an area close to the skin surface of a patient 1. According to one example, the second distal optical device 85 is a Dermatoscope. The second distal optical device 85 may comprise a glass plate coming into contact with the skin. According to one embodiment, the second distal optical device 85 may comprise a polarized light emitter so as to obtain depth image information of the epidermis.

To this end, the last branch 65 of the robot arm 6 or the distal operator device 8 may be equipped with a force return sensor in order to slow its travel from the second distal optical device 85, or even stop and stabilize it. When the second distal optical device 85 is in contact with the skin of a patient 1, the triggering of a camera may be engaged.

According to another example, each axis of the robot arm 6 is equipped with a force sensor. Analysis of the force values recorded on the sensors is used to enslave the pressure applied to the surface. Thus, the robot arm 6 thanks to its torque sensors in each axis makes it possible to enslave a contact pressure between a tool and the work surface, in this case the skin of a patient. This can also be used to "slide" the tool on a work surface.

According to one embodiment, a sweeping device 89 is activated in order to move away hairs from the optic 85. Such a scanning device 89 may be automatically implemented when stabilizing the optic of the second distal optical device 85. One benefit is to avoid taking an image of hair located close to a singularity of which it is wished to take an image. The sweeping device 89, according to one embodiment, comprises a rotating rod that activates flexible brushes near to the optic 85 or a pneumatic system. One advantage is that the hair is turned so that it does not remain between the optic 85 and the skin. According to one embodiment, a plurality of scanning devices 89 is arranged around the optic 85. FIG. 6B shows two of them.

When the second optic 85 has captured one or more images with a more precise resolution of the singularity, the second device 85 may perform a retract movement to return to its initial position. The robot arm 6 can then continue its travel and resume the guiding trajectory that has been planned.

According to one example, the guiding is performed at a distance of between 1 cm and 20 cm from the surface of a patient's body 1. According to a preferential embodiment, the guiding is performed at a distance of between 2 cm and 8 cm from the skin surface.

Further, the distal operator device 8 may comprise one or more transmitters of the ultrasonic, radiofrequency or laser type or any other source of signals capable of being used to generate an incident beam. According to one embodiment, the distal operator device 8 may comprise a focused transmitter network and means of controlling the direction and power transmitted.

Figure 8:
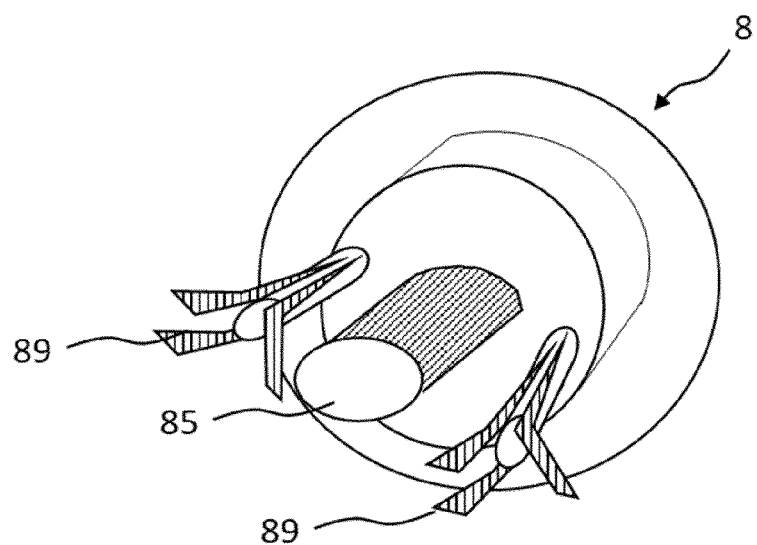
FIG. 8: a second example of the head of a robotic arm of the robot device of the invention.

According to another configuration, the distal operator device 8 comprises a laser device. This embodiment may also be compatible with the presence of an optic not shown in FIG. 8.

When an ultrasonic transmitter is arranged at the end of the distal operator device 8, an ultrasonic receiver can be combined to measure the reflected signal so as to construct an image of the dermis and/or an image of a patient's skin thickness, or even an image of a vessel or an organ.

Screen

According to one embodiment, the robot device 1 comprises a screen 4 making it possible to display the body model MOD_P of the patient reconstructed from the images acquired by the acquisition system 3'. In this way, an operator can visualize the three-dimensional model of the patient and its position in space. This visualization allows an operator to preset the robot device 1 of the invention, for example the orientations of the optical devices 3 or the position of the robot device 1 or even a default position of the robot arm 6.

According to one embodiment, the screen 4 is touch-sensitive. It may comprise the generation of digital buttons making it possible to control or configure the robot device 1 or robot arm 6. According to one example, a stop button is accessible. According to another embodiment, mechanical or optical actuators may alternatively be arranged on the robot device 1 of the invention so that they are directly accessible without having to interact with the screen 4. According to an example, an emergency stop button is positioned on the robot device 1 to stop movements of the robot arm 6.

According to an example, a movement on the robot arm stops it. According to this configuration, the robot arm 6 comprises a haptic sensor to discriminate a pressure or a force applied to the body of the robot arm 6. When a force threshold is measured, the robot arm 6 is immediately immobilized before resuming its travel from a new start or resume command received from the user interface.

The invention claimed is:

1. A robot device ensuring an automatic guiding of a robotic arm, the robot device comprising:
    a frame holding a robotic arm articulated along a plurality of axes of freedom, said robotic arm comprising a distal operator device for generating a human-machine interaction,
    an image acquisition system comprising at least two optical devices integral with said frame and arranged in at least two distinct positions of the frame, each optical device being configured to acquire a 3D image, the image acquisition system being configured to acquire a plurality of 3D images of a human body of a patient from the at least two optical devices, and
    a calculation unit for generating in real time a human body model of said patient from said acquired 3D images and a guiding trajectory referenced to the surface of said human body model,
    wherein movements of said robotic arm are enslaved to said guiding trajectory, and
    wherein the frame comprises a main body and a base, said main body holding the image acquisition system and said base being provided with means of displacement to make the robot device movable.

2. The robot device according to claim 1, wherein:
    at least one first optical device of the at least two optical devices comprises a first linear arrangement of at least two cameras along a first axis;
    at least one second optical device of the at least two optical devices comprises a second linear arrangement of at least two cameras along a second axis.

3. The robot device according to claim 1, wherein at least one optical device of the at least two optical devices comprises a means of orienting an acquisition axis by actuating a mechanical link.

4. The robot device according to claim 1, wherein each optical device comprises:
    at least two infrared cameras and/or;
    at least one color camera and/or;
    at least one pair of color cameras configured to generate 3D images by stereoscopy and/or;
    at least three cameras comprising two infrared cameras and one color camera and/or;
    at least one infrared projector projecting a pattern and two infrared cameras capturing said pattern projected onto the surface of a human body; and/or
    at least one light projector projecting patterns of structured light and at least one camera capturing said patterns; and/or
    a time-of-flight camera and/or;
    a laser transceiver device.

5. The robot device according to claim 1, wherein the at least two optical devices are arranged to cover a field of view related to the image acquisition system such that the image acquisition system has a virtual origin that is displaced out of a plane comprising origins of the at least two optical devices.

6. The robot device according to claim 1, wherein:
    the at least two optical devices are distanced in a horizontal plane of a Cartesian coordinate system with a distance comprised in the range [30 cm and 100 cm];
    the at least two optical devices are distanced in a vertical axis from a Cartesian coordinate system with a distance between the range [30 cm and 100 cm].

7. The robot device according to claim 1, further comprising at least one electronic device for generating from the images acquired by the acquisition system a point cloud representing a three-dimensional surface of a patient's body.

8. The robot device according to claim 7, wherein the at least one electronic device is configured to generate a global point cloud from a plurality of point clouds generated from each 3D image acquired by each optical device, said global point cloud comprising a compilation of points of each point cloud.

9. The robot device according to claim 7, wherein the at least one electronic device is configured to generate, from images acquired by the acquisition system, instructions for guiding movements of the robotic arm.

10. The robot device according to claim 7, wherein the at least one electronic device is configured to generate a first 3D model of a surface of all or part of a human body, said first 3D model comprising a mesh, said first 3D model being used to calculate a first guiding trajectory on a surface of the first 3D model, and to calculate a first movement of the robotic arm.

11. The robot device according to claim 10, wherein the at least one electronic device is configured to generate in real time, from images acquired by the acquisition system, a new 3D model of a surface of all or part of a human body, said new 3D model comprising a mesh, said new 3D model being generated at regular intervals and being used to recalculate in real time a new guiding trajectory on the surface of the new 3D model, and to recalculate in real time a new movement of the robotic arm.

12. The robot device according to claim 1, wherein the robotic arm comprises at least 5 portions, each portion extending along an axis and pivoting with respect to at least one axis of another portion by means of a pivot link, the pivoting of all the pivot links driving a movement of the robotic arm.

13. The robot device according to claim 1, wherein the robot device is configured to implement self-calibration of the optical devices of the acquisition system with respect to a reference optical device of said acquisition system.

14. A robot device ensuring an automatic guiding of a robotic arm, the robot device comprising:
    a frame holding a robotic arm articulated along a plurality of axes of freedom, said robotic arm comprising a distal operator device for generating a human-machine interaction,
    an image acquisition system comprising at least two optical devices integral with said frame and arranged in at least two distinct positions of the frame, each optical device being configured to acquire a 3D image, the image acquisition system being configured to acquire a plurality of 3D images of a human body of a patient from the at least two optical devices, and
    a calculation unit for generating in real time a human body model of said patient from said acquired 3D images and a guiding trajectory referenced to the surface of said human body model, wherein movements of said robotic arm are enslaved to said guiding trajectory, wherein each optical device comprises
- a first set of optical devices comprising a first field of view between 30° and 70° vertically and between 50 and 100° horizontally; and
- a second set of optical devices having a second field of view between 50° and 100° vertically and between 30 and 70° horizontally.

15. A robot device ensuring an automatic guiding of a robotic arm, the robot device comprising:
- a frame holding a robotic arm articulated along a plurality of axes of freedom, said robotic arm comprising a distal operator device for generating a human-machine interaction,
- an image acquisition system comprising at least two optical devices integral with said frame and arranged in at least two distinct positions of the frame, each optical device being configured to acquire a 3D image, the image acquisition system being configured to acquire a plurality of 3D images of a human body of a patient from the at least two optical devices, and
- a calculation unit for generating in real time a human body model of said patient from said acquired 3D images and a guiding trajectory referenced to the surface of said human body model, wherein movements of said robotic arm are enslaved to said guiding trajectory,
- wherein the frame comprises a screen for displaying a 3D image of the body of an individual from at least one of the at least two optical devices.

* * * * *